US008256422B2

(12) United States Patent
Brewer et al.

(10) Patent No.: US 8,256,422 B2
(45) Date of Patent: Sep. 4, 2012

(54) RESPIRATORY ACCESS PORT ASSEMBLY WITH PASSIVE LOCK AND METHOD OF USE

(75) Inventors: John Brewer, Marietta, GA (US); Cassandra E. Morris, Roswell, GA (US); Joe Gordon, Mansfield, MA (US); David Zitnick, Providence, RI (US)

(73) Assignee: Kimberly-Clark Worldwide, Inc, Neenah, WI (US)

( * ) Notice: Subject to any disclaimer, the term of this patent is extended or adjusted under 35 U.S.C. 154(b) by 711 days.

(21) Appl. No.: 12/466,697

(22) Filed: May 15, 2009

(65) Prior Publication Data

US 2010/0288282 A1   Nov. 18, 2010

(51) Int. Cl.
*A61M 16/00* (2006.01)

(52) U.S. Cl. ............... 128/207.14; 128/207.16; 604/317

(58) Field of Classification Search ............. 128/200.26, 128/202.27, 205.24, 207.14–207.16; 604/35, 604/119, 163, 171
See application file for complete search history.

(56) References Cited

U.S. PATENT DOCUMENTS

| | | | | |
|---|---|---|---|---|
| 4,270,778 A | * | 6/1981 | Brownell | 285/305 |
| 4,326,520 A | * | 4/1982 | Alley | 604/171 |
| 4,569,344 A | * | 2/1986 | Palmer | 128/207.16 |
| 4,641,646 A | * | 2/1987 | Schultz et al. | 128/207.14 |
| 4,836,199 A | * | 6/1989 | Palmer | 128/207.16 |
| 5,158,569 A | * | 10/1992 | Strickland et al. | 604/533 |
| 5,207,641 A | | 5/1993 | Allton | |
| 5,255,672 A | * | 10/1993 | Jinotti | 128/200.26 |
| 5,309,902 A | | 5/1994 | Kee et al. | |
| 5,333,606 A | * | 8/1994 | Schneider et al. | 128/200.24 |
| 5,333,607 A | | 8/1994 | Kee et al. | |
| 5,335,655 A | | 8/1994 | Kee | |
| 5,337,780 A | | 8/1994 | Kee | |
| 5,343,857 A | | 9/1994 | Schneider et al. | |
| 5,354,267 A | | 10/1994 | Niermann et al. | |
| 5,357,946 A | | 10/1994 | Kee et al. | |
| 5,377,672 A | * | 1/1995 | Kee | 128/207.16 |
| 5,445,141 A | | 8/1995 | Kee et al. | |
| 5,540,668 A | * | 7/1996 | Wilson et al. | 604/248 |

(Continued)

FOREIGN PATENT DOCUMENTS

DE   29 39 794 A1   4/1981

(Continued)

*Primary Examiner* — Stephen Crow
(74) *Attorney, Agent, or Firm* — James B. Robinson; Sue C. Watson

(57) ABSTRACT

A respiratory access assembly includes a distal plate having a port, which is adapted to be positioned in operable communication with an artificial airway of a patient. The assembly includes a distal plate having a port and a proximal plate which has a first port and a second port. The distal plate is positioned against the proximal plate in a stacked configuration, and each plate is configured to move relative to the other. The assembly has an actuator which is positioned adjacent to at least one plate. The actuator cooperates with both plates to substantially prevent movement of the plates when the port of the distal plate is positioned in an alignment with at least one port of the proximal plate and an object, such as a suction catheter, is positioned through the aligned ports of the plates. The actuator cooperates with at least one plate to permit movement of at least one plate when (a) no object is positioned through aligned ports, and (b) when no ports are aligned. The assembly desirably has predetermined positions, which include a first open position, a second open position, and a third closed position.

8 Claims, 9 Drawing Sheets

U.S. PATENT DOCUMENTS

| | | | |
|---|---|---|---|
| 5,628,306 A | 5/1997 | Kee | |
| 5,643,294 A * | 7/1997 | Tovey et al. | 606/148 |
| 5,694,922 A * | 12/1997 | Palmer | 128/202.27 |
| 5,730,123 A * | 3/1998 | Lorenzen et al. | 128/207.14 |
| 5,735,271 A | 4/1998 | Lorenzen et al. | |
| 5,738,091 A | 4/1998 | Kee et al. | |
| 5,746,199 A * | 5/1998 | Bayron et al. | 128/205.24 |
| 5,882,348 A | 3/1999 | Winterton et al. | |
| 5,916,201 A | 6/1999 | Wilson, Jr. et al. | |
| 6,012,451 A | 1/2000 | Palmer | |
| 6,070,582 A * | 6/2000 | Kee | 128/207.16 |
| D448,842 S * | 10/2001 | Madsen et al. | D24/112 |
| D448,843 S * | 10/2001 | Madsen et al. | D24/112 |
| D449,106 S * | 10/2001 | Madsen et al. | D24/129 |
| D449,107 S * | 10/2001 | Madsen et al. | D24/129 |
| 6,494,203 B1 | 12/2002 | Palmer | |
| 6,543,451 B1 * | 4/2003 | Crump et al. | 128/207.14 |
| 6,609,520 B1 * | 8/2003 | Carlsen et al. | 128/207.14 |
| 6,612,304 B1 * | 9/2003 | Cise et al. | 128/200.26 |
| 6,615,835 B1 * | 9/2003 | Cise et al. | 128/207.14 |
| 6,629,530 B2 * | 10/2003 | Cise | 128/205.24 |
| 6,698,424 B2 | 3/2004 | Madsen et al. | |
| 6,729,326 B1 | 5/2004 | Winterton et al. | |
| 6,811,142 B2 | 11/2004 | Svendsen | |
| 6,923,184 B1 * | 8/2005 | Russo | 128/207.14 |
| 6,978,783 B2 * | 12/2005 | Svendsen | 128/207.14 |
| 7,021,313 B1 | 4/2006 | Crump et al. | 128/207.14 |
| 7,188,623 B2 * | 3/2007 | Anderson et al. | 128/207.16 |
| 7,191,782 B2 | 3/2007 | Madsen | |
| 7,263,997 B2 | 9/2007 | Madsen et al. | |
| 7,353,822 B2 * | 4/2008 | van Hooser et al. | 128/202.27 |
| 2004/0221852 A1 * | 11/2004 | Madsen | 128/207.14 |
| 2005/0199243 A1 * | 9/2005 | Svendsen | 128/207.14 |
| 2010/0147310 A1 * | 6/2010 | Brewer et al. | 128/207.14 |
| 2010/0288282 A1 * | 11/2010 | Brewer et al. | 128/207.14 |

FOREIGN PATENT DOCUMENTS

| | | |
|---|---|---|
| DE | 40103300.0001 | 8/2001 |
| DE | 40103300.0002 | 8/2001 |
| DE | 40103300.0003 | 8/2001 |
| DE | 40103300.0004 | 8/2001 |
| EP | 1 208 865 A2 | 5/2002 |
| EP | 0 812 220 B1 | 5/2004 |
| EP | 0 805 694 B1 | 6/2007 |
| FR | 000012046.0001 | 8/2001 |
| FR | 000012048.0001 | 8/2001 |
| FR | 000012049.0001 | 8/2001 |
| FR | 000012050.0001 | 8/2001 |
| GB | 1 443 152 A | 7/1976 |
| GB | 2 061 465 A | 5/1981 |
| GB | 002100746 | 8/2001 |
| GB | 002100747 | 8/2001 |
| GB | 002100748 | 8/2001 |
| GB | 002100749 | 8/2001 |
| WO | WO 93/21981 A2 | 11/1993 |
| WO | WO 95/31240 A1 | 11/1995 |
| WO | WO 95/31249 A1 | 11/1995 |
| WO | WO 95/31250 A1 | 11/1995 |
| WO | WO 96/22118 A1 | 7/1996 |
| WO | WO 96/26757 A1 | 9/1996 |
| WO | WO 98/10808 A2 | 3/1998 |
| WO | WO 98/33536 A1 | 8/1998 |
| WO | WO 99/19013 A1 | 4/1999 |
| WO | WO 01/21241 A1 | 3/2001 |
| WO | WO 01/76659 A1 | 10/2001 |
| WO | WO 01/76673 A1 | 10/2001 |
| WO | WO 02/28463 A2 | 4/2002 |
| WO | WO 02/051485 A1 | 7/2002 |
| WO | WO 2004/101044 A1 | 11/2004 |
| WO | WO 2006/133882 A1 | 12/2006 |
| WO | WO 2007/141487 A1 | 12/2007 |

* cited by examiner

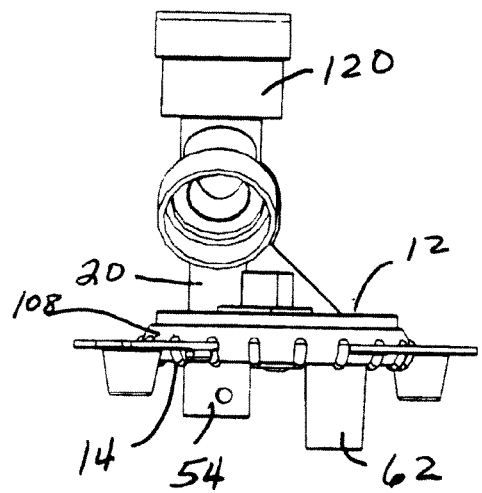
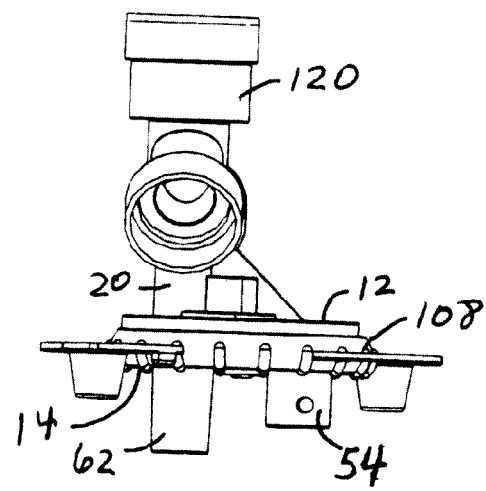
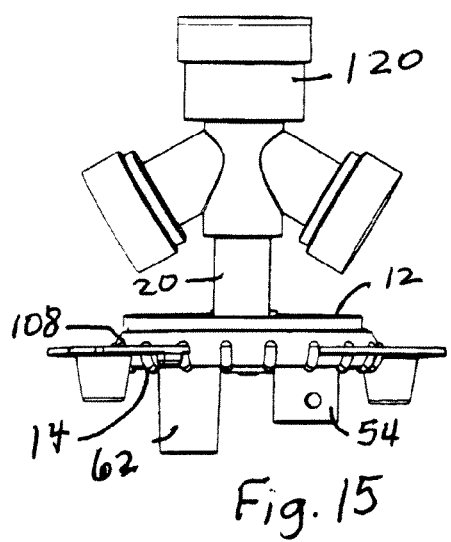

RESPIRATORY ACCESS PORT ASSEMBLY WITH PASSIVE LOCK AND METHOD OF USE

BACKGROUND

The inventions disclosed herein relate generally to improved medical care for intubated patients, and more particularly to a novel multiple access respiratory port, assembly, manifold, fitting, adaptor, connector and/or access control assembly inventions, and related methods, for ventilating, aspirating, monitoring, sampling, and providing therapeutic delivery to the respiratory tracts of intubated patients, including infants, adolescents, and adults.

Respiratory patient care is a dynamically developing field in medicine, ranging in its needs from infants to the aged. The range of respiratory ailments, both temporary and permanent, to which such patients are subjected, are many and varied. For example, the range of procedures for intubated patients may include the following: ventilation, aspiration, oxygenation, sampling, visual inspection, in-line sensing, pressure monitoring, flushing, medicating and/or lavage. Most problems now center or focus on multiple needs of the patient and accommodation of multiple treatments, some to be performed at the same time. The lack of equipment to facilely, efficiently, and safely accomplish the multiple therapies in the best interest of the patient has been and continues to be a concern.

For example, in low lung capacity patients, such as premature babies and adults suffering from emphysema, one problem is the removal of accumulated lung secretions. It is undesirable to starve such patients of oxygen during the secretion removal process. Secretion removal is accomplished via a suction catheter which is temporarily positioned via a respiratory access assembly in an artificial airway, i.e., an endotracheal tube placed in a portion of the patient's respiratory tract to provide air (oxygen and other gases) to the lungs of such patients. While this procedure sounds simple, it is fraught with difficulties, particularly when a caregiver must change devices or perform other therapeutic treatments sequentially or simultaneously. In fact, these difficulties may result in the patient contracting ventilator acquired pneumonia. There is a need to address and overcome these difficulties.

SUMMARY OF THE INVENTION

In response to the difficulties and problems discussed herein, a respiratory access assembly is provided. The respiratory access assembly comprises a distal plate having a port. The port is adapted to be positioned in operable communication with an artificial airway of a patient. The assembly includes a proximal plate, which has a first port and a second port. The distal plate is positioned against the proximal plate in a stacked configuration, and each plate is configured to move. The assembly also has an actuator which is positioned adjacent to at least one plate. The actuator cooperates with both plates to substantially prevent movement of the plates when the port of the distal plate is positioned in an alignment with at least one port of the proximal plate and an object is positioned through the aligned ports of the plates. The actuator cooperates with at least one plate to permit movement of at least one plate when (a) no object is positioned through aligned ports, and (b) when no ports are aligned.

In another aspect of the invention, a method of using a respiratory access assembly is provided. The method includes providing a respiratory access assembly. The respiratory access assembly includes a distal plate having a port. The port is adapted to be positioned in operable communication with an artificial airway of a patient. The assembly also includes a proximal plate which has a first port and a second port. The distal plate is positioned against the proximal plate in a stacked configuration. The distal plate and the proximal plate are configured to move relative to each other. The assembly further includes an actuator positioned adjacent to at least one plate. The actuator cooperates with both plates to substantially prevent movement of the plates when the port of the distal plate is positioned in an alignment with at least one port of the proximal plate and an object is positioned through the aligned ports of the plates. The actuator cooperates with at least one plate to permit movement of at least one plate when (a) no object is positioned through aligned ports, and (b) when no ports are aligned. The method also includes moving one of more plate so that the port of the distal plate is aligned with a port of the proximal plate to provide an opened assembly. The method further includes moving an object through the opened assembly, such that contact of the object against a portion of the actuator activates at least the portion of the actuator such that the actuator locks the plates in a position which substantially prevents movement of the plates.

BRIEF DESCRIPTION OF THE DRAWINGS

FIG. 13 is a side view of a first open position of the assembly with the port of the distal plate and the first port of the proximal plate in axial alignment;

FIG. 14 is a side view of a second open position of the assembly with the port of the distal plate and the second port of the proximal plate in axial alignment; and FIG. 15 is a side view of a third closed position of the assembly in which the port of the distal plate, the first port of the proximal plate and the second port of the proximal plate are not aligned and are blocked.

DETAILED DESCRIPTION OF THE INVENTION

Figure 1:
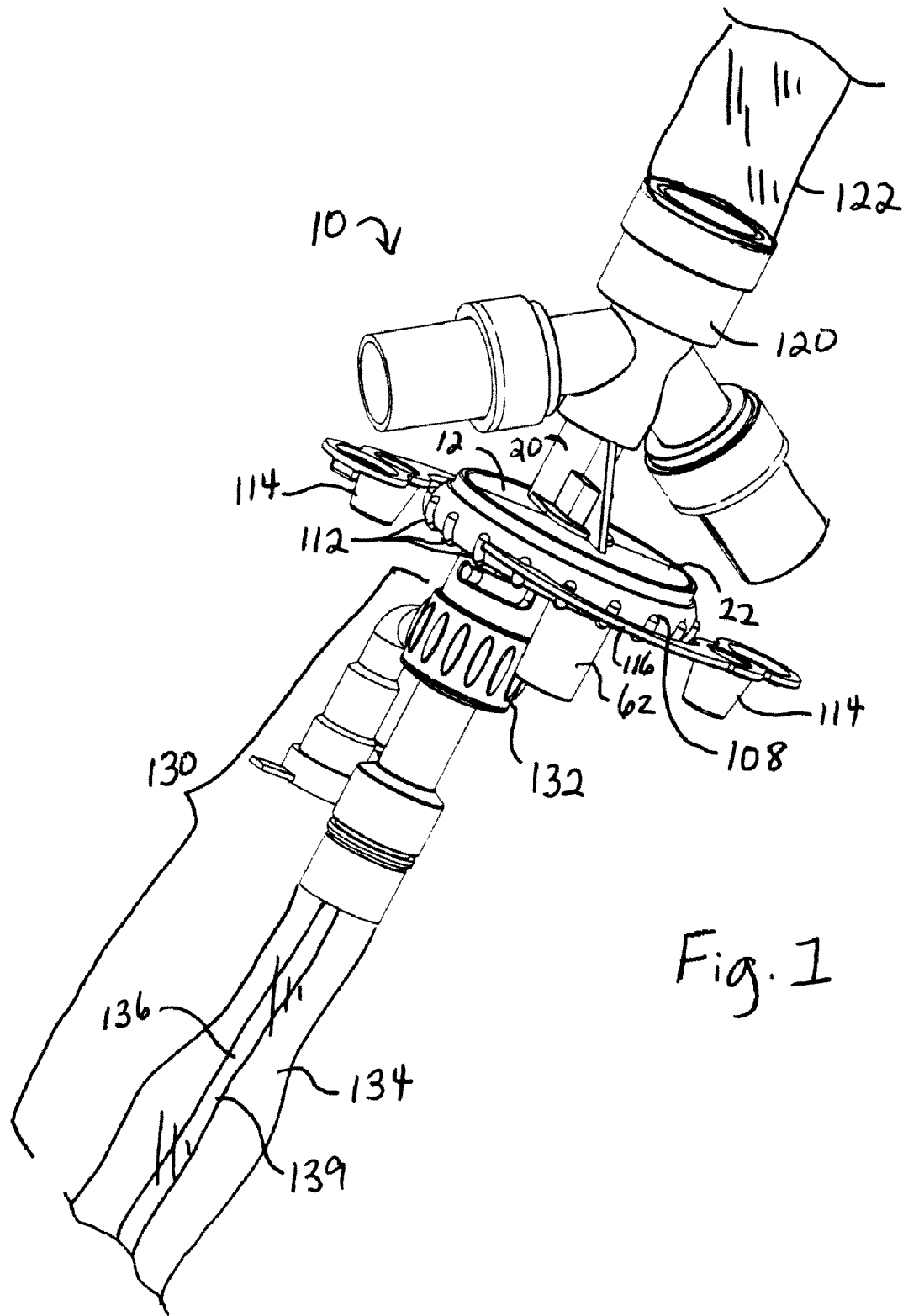
FIG. 1 is a perspective view of a respiratory access assembly of the present invention, illustrating the assembly coupled to a respiratory manifold which is connected to an artificial airway at a distal end of the assembly, and showing a portion of a suction catheter assembly coupled to a proximal end of the respiratory access assembly.

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

The present respiratory access port assembly operates in a closed ventilating system and is designed to accommodate multiple access to the respiratory system of an intubated patient without compromising the closed circuit character of the closed system and without interruption of the flow of ventilating gases to the patient. Access to the closed respiratory system through one or more access sites is provided, for example, but not by way of limitation, to ventilate the lungs of the patient with gas or gases, to aspirate secretions from the lungs, to oxygenate the lungs to eliminate or reduce residual carbon dioxide therefrom, to visually inspect selected parts of the patient's respiratory system, to sample sputum and gases, to sense parameters such as flow rates, pressure, and/or temperature, to flush with solution(s), and to administer medication, gases, and/or lavage.

Many current designs for respiratory access port assemblies may have only one port. In these instances, the suction catheter must be removed when other tasks need to be performed, such as, for example, bronchoscopy, bronchial alveolar lavage, and so forth. Opening a closed ventilating system by removing the suction catheter on such a ventilated patient can lead to infection, as noted previously. Also, current designs of multiple access port manifolds and/or assemblies do not contain a safety lock. In certain instances, due to the lack of such a safety lock, the introduction of a suction catheter through a manifold port may result in a portion of the catheter being guillotined or cut off and aspirated into the patient's lungs. This can lead to significant complications, including airway blockage, infection, and even death. Further, failure to adequately seal a respiratory access assembly may cause a compromise of positive end-expiration pressure (PEEP), which in turn may cause suboptimal ventilation which can result in collapsing alveoli in the patient's lungs. The present respiratory access assembly includes features which permit multiple access without opening the closed ventilation system, and it contains a passive safety lock feature which prevents loss of any portion of the suction catheter and/or other object while it is positioned within the assembly.

Turning now to the drawings, as illustrated in FIGS. 1-15, a respiratory access assembly 10 is provided. The assembly 10, as shown in FIGS. 1-9, includes a distal disk or plate 12 and a proximal disk or plate 14 which are positioned next to each other in a stacked and axially aligned configuration. The terms "align," "alignment," and variations thereof desirably, but not by way of limitation, refer to the spatial property possessed by an arrangement or position of things in a straight line. The terms "configure" or "configuration", and derivatives thereof desirably, but not by way of limitation, refer to the design, arrangement, set up, or shape with a view to specific applications or uses. For example: a military vehicle that was configured for rough terrain; configured the computer by setting the system's parameters.

The distal disk or plate 12 includes at least one port 16 having an opening formed through the disk or plate 12, as illustrated in FIGS. 2 and 4-6. A cuff, such as cuff 20, may, for example, but not by way of limitation, be provided on an outer distal surface 22 of the disk or plate 12. Such a cuff 20 generally encircles the port 16 and the opening extends therethrough, such that the cuff 20 provides a portion of the port 16. It will be understood that any cuff(s) shown and/or described herein, whether on an inner or outer surface of a disk or plate, desirably include the characteristics and features described herein for cuff 20.

The term "port" as used herein desirably, but not by way of limitation, means an opening into or through a component for the passage of an object and/or a liquid and/or a gas. The term "cuff" as used herein also desirably, but not by way of limitation, means a generally cylindrical component having an opening therethrough which is positioned over a port and forms a portion of the port. Further, it will be understood that a port and its cuff may collectively be given the term herein of "port", and two or more ports, each with its associated cuff, may collectively be given the term herein of "ports".

The term "plate" as used herein desirably, but not by way of limitation, refers to any shape and configuration of a plate, including, but not limited to, round, square, rectangular, and so forth. It will be appreciated that the plate may be arced, arched, planar, convex, concave, and so forth.

The distal disk or plate 12 also has a proximal surface 24 which includes an outer perimeter 26 and a perimeter wall 28 which is desirably formed along the outer perimeter 26. The perimeter wall 28 may extend proximally away from the outer perimeter 26 at about a 90 degree angle. The term "about" desirably, but not by way of limitation, when placed adjacent a number/numeral, refers to the stated number plus or minus ten (10) percent of the stated number. An inner surface 30 of the perimeter wall 28 desirably has a plurality of teeth 32 formed thereon. The plurality of teeth 32 may be positioned adjacent the port 16. The perimeter wall 28 also desirably includes an outer surface 34 which has a groove 36 formed therein. An O-ring 38 may be positioned in the groove 36. The O-ring 38 serves as at least a partial seal when it is positioned against a perimeter wall of the proximal disk 14. The proximal surface 24 of the distal plate 12 includes a center aperture 40 configured to receive a fastener, such as a screw or pin 42 therethrough (shown in FIGS. 11 and 12). The pin 42 desirably holds the distal and proximal plates 12, 14 adjacent each other in a stacked and axially aligned position, while permitting movement of each plate 12, 14 relative to the other. A semi-circular indentation 44 surrounds the center aperture 40. This semi-circular indentation 44 cooperates with other components and may limit the movement of the distal and proximal plates 12, 14 relative to each other. In this embodiment, but not by way of limitation, the rotation is desirably limited to a range of about less than 200 degrees. More desirably, the rotation is limited to a range of between about 1 degree and about 200 degrees.

The inner proximal surface 24 of the distal plate 12 also may include a plurality of ramped indentations 46. These ramped indentations desirably cooperate with other components described herein to assist in holding the plates 12, 14 in specific, predetermined positions relative to each other. Such components and predetermined positions will be discussed in detail below.

The terms "orientation" or "position" used interchangeably herein desirably, but not by way of limitation, refer to the spatial property of a place where or way in which something is situated; for example, "the position of the hands on the clock."

Figure 7:
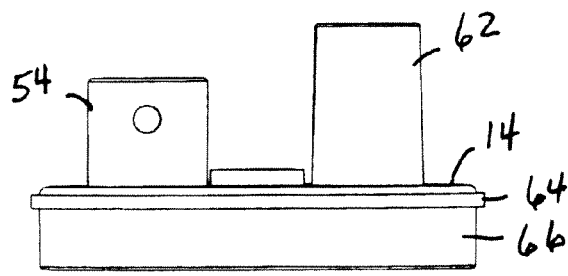
FIG. 7 is a side view of the proximal plate of the respiratory access assembly of FIGS. 1-3.
Figure 8:
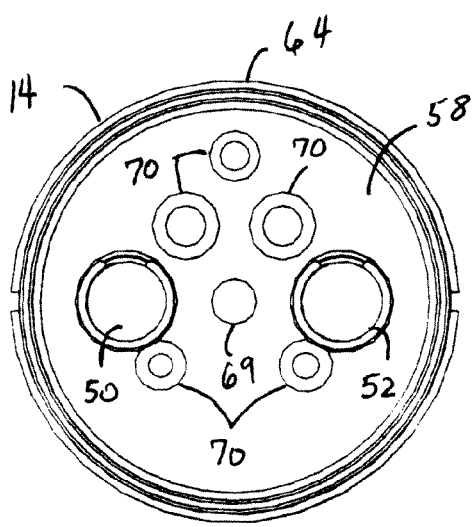
FIG. 8 is a plan view of the distal surface of the proximal plate shown in FIG. 7.
Figure 9:
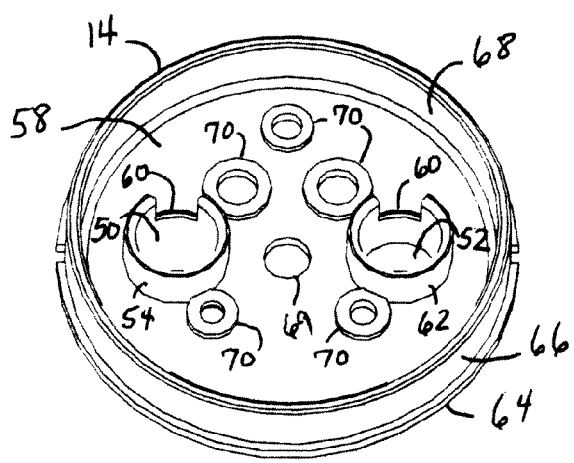
FIG. 9 is a perspective view of the distal surface of the proximal plate of FIGS. 7 and 8.

The proximal disk or plate 14 includes, but not by way of limitation, a first port 50 and a second port 52, each having an opening extending through the proximal plate 14, as shown in FIGS. 7-9. The first port 50 may have a first cuff 54 which is provided on an outer proximal surface 56 of the proximal plate 14. In this instance, as illustrated in FIG. 9, the first cuff 54 extends beyond an inner distal surface 58 as well, and may include a notch 60 therein. Similarly, the second port 52 may have a second cuff 62 which is provided on the outer proximal surface 56 of the proximal plate 14. The second cuff 62, like the first cuff 54, also extends beyond the inner distal surface 58, and may also include a notch 60 therein as well.

The proximal plate 14 has an outer perimeter 64 which desirably includes a perimeter wall 66. The perimeter wall 66 may be formed along the outer perimeter 64 and it desirably extends distally away from the outer perimeter 64 at about a 90 degree angle. In the present embodiment, but not by way of limitation, the perimeter wall 28 of the distal plate 12 is sized to fit within the perimeter wall 66 of the proximal plate 14, such that the O-ring 38 on the outer surface 34 of the perimeter wall 28 of the distal plate 12 at least assists in forming a movable seal against an inner surface 68 of the perimeter wall 68 of the proximal plate 14.

A center opening 69 is provided in the proximal plate 14. The center opening 69 desirably aligns with the center aperture 40 in the distal plate 12, and both are held at least adjacent each other by the screw or pin 42 (FIGS. 11 and 12) positioned therethrough.

A plurality of protuberances, such as the plurality of raised circular ribs 70, may be provided adjacent the center opening 69 and the cuffs 54, 62 on the distal surface 58 of the proximal plate 14. At least a portion of a passive lock assembly or a means for locking the distal and proximal plates together may be positioned adjacent to the distal surface 58 of the proximal plate 14.

Figure 2:
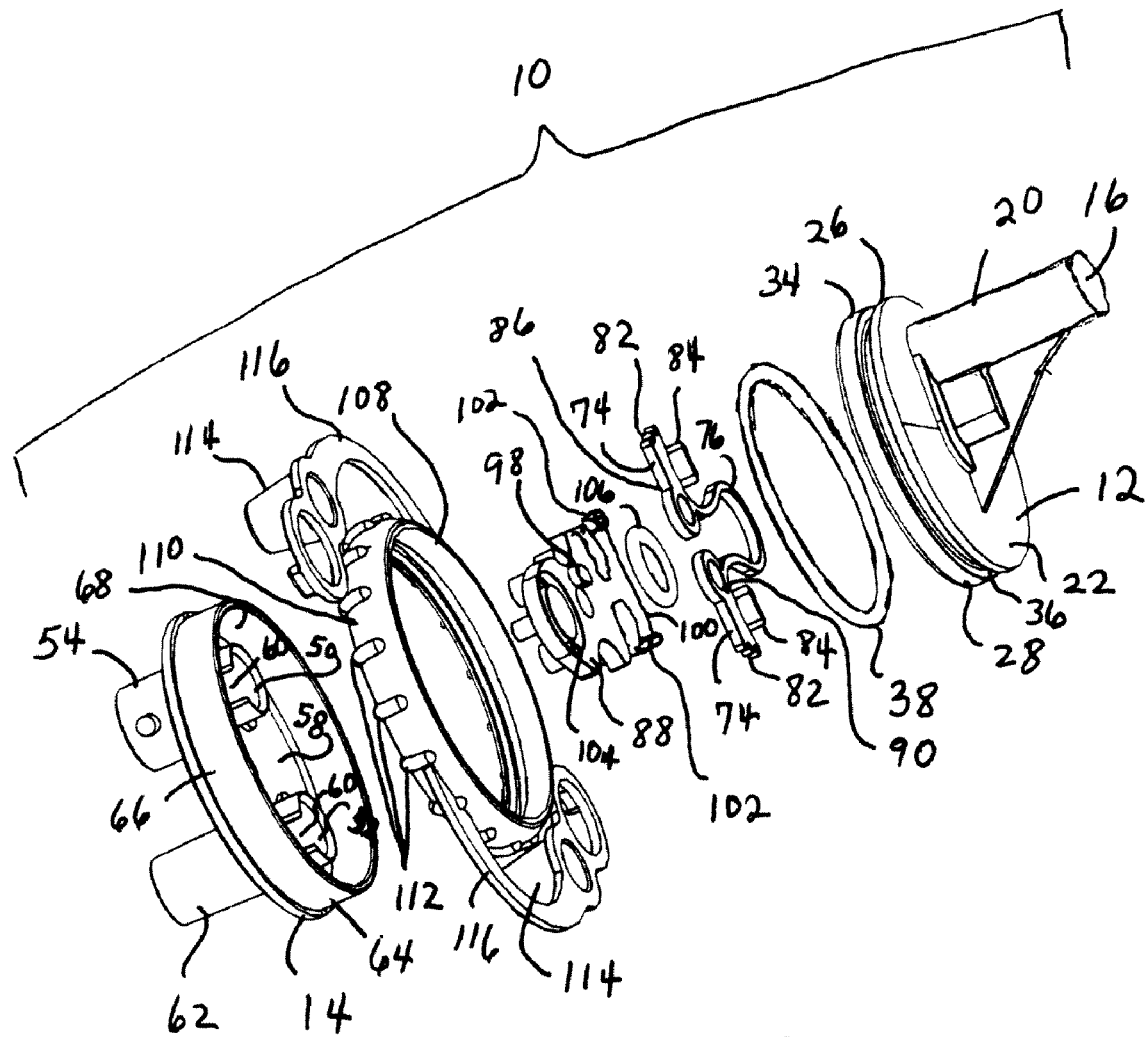
FIG. 2 is an exploded distal perspective view of the respiratory access assembly of FIG. 1.
Figure 3:
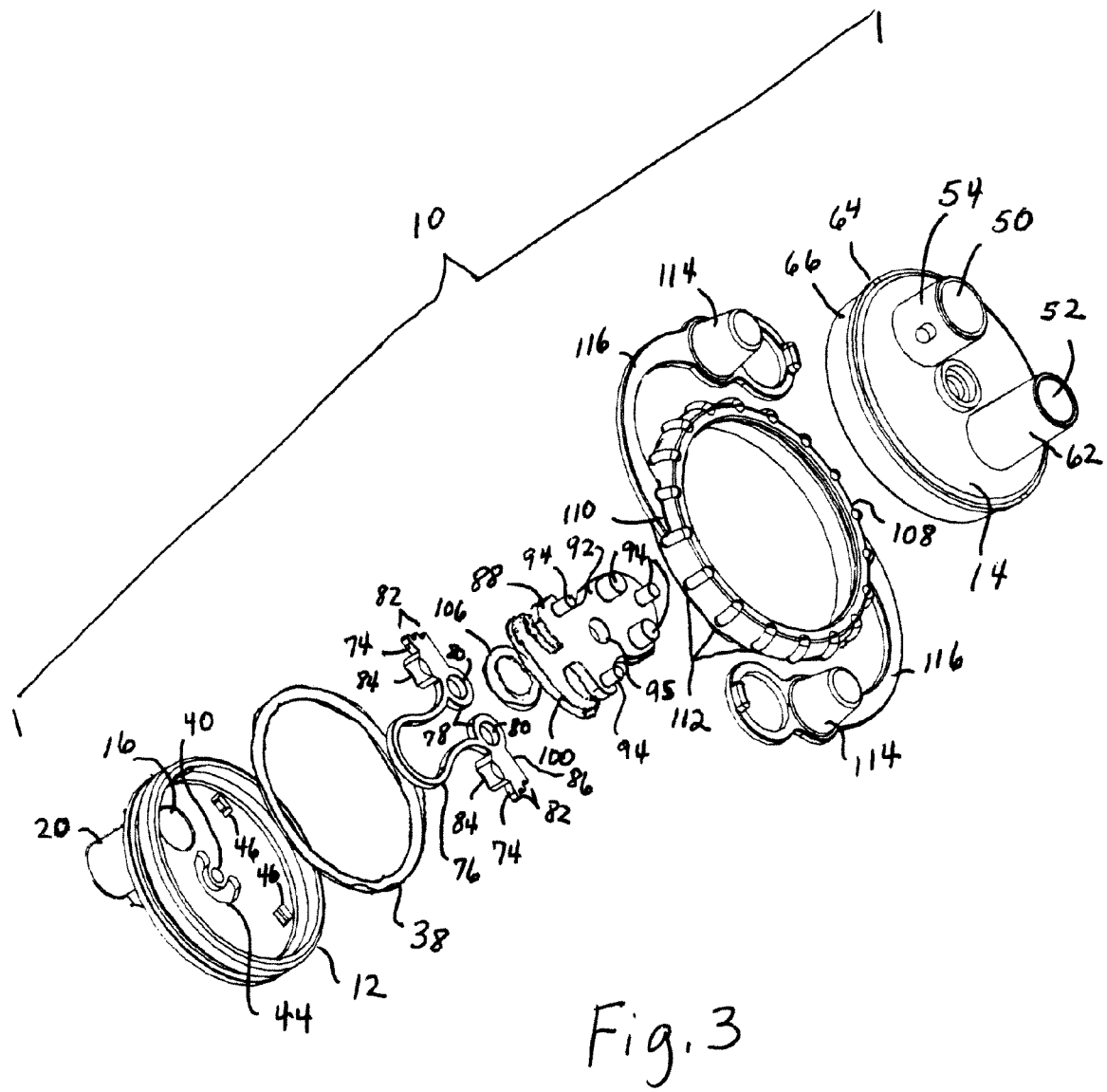
FIG. 3 is an exploded proximal perspective view of the respiratory access assembly of FIGS. 1 and 2.
Figure 4:
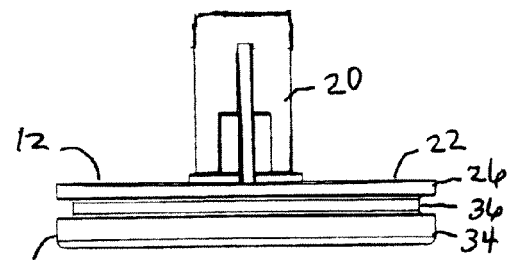
FIG. 4 is a side view of a distal plate of the respiratory access assembly of FIGS. 1-3.
Figure 5:
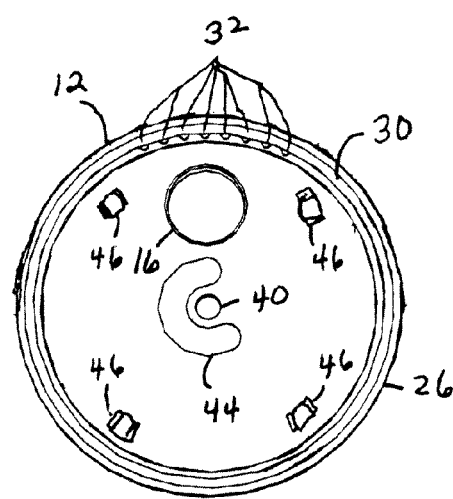
FIG. 5 is a plan view of the proximal surface of the distal plate shown in FIG. 4.
Figure 6:
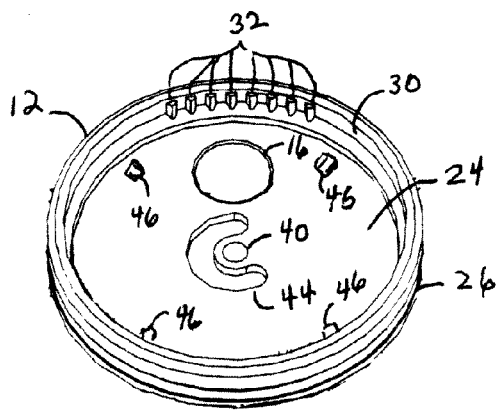
FIG. 6 is a perspective view of the proximal surface of the distal plate shown in FIGS. 4 and 5, showing a row of teeth positioned on a portion of the plate.
Figure 10A:
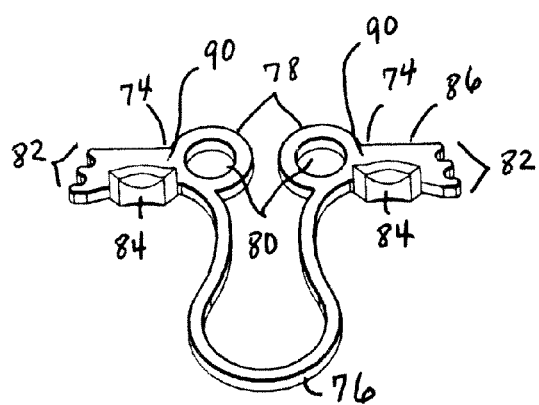
FIGS. 10A and 10B are perspective views of the pair of pawls (FIG. 10A) and the base (FIG. 10B), respectively, showing the distal surface of each.

An actuator or passive lock assembly desirably includes, for example, but not by way of limitation, a pair of pawls 74 attached by a U-shaped connector 76, as illustrated in FIGS. 2, 3, and 10A. The pawls 74 and connector 76 are desirably positioned on the distal surface 58 of the proximal plate 14. At one end, the pawls 74 each have a circular portion 78 with an opening 80 therein. At an opposite end, each pawl 74 has a plurality of teeth 82. Each pawl 74 also desirably includes a flange 84 positioned along an outer edge 86 thereof. The flange 84 on each of the pair of pawls 74 is configured to moveably extend into the notch 60 in the first cuff 54 and the notch 60 in the second cuff 62, respectively. In this manner, the flange 84 of one of the pawls 74 extends into the first cuff 54 and slightly into the first port 50. Similarly, the flange 84 of another of the pawls 74 extends into the second cuff 62 and slightly into the second port 52. Each flange 84 is desirably moveable out of its respective notch 60 when an object, such as, for example, but not by way of limitation, a suction catheter, is positioned through the first or second port 50, 52.

Figure 10B:
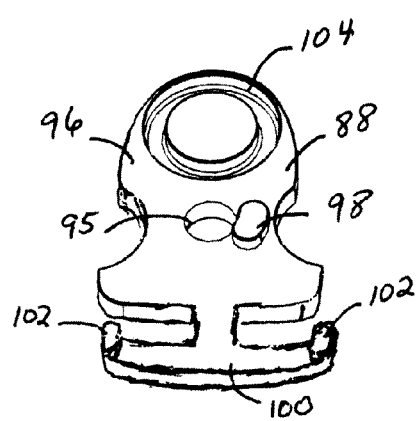

A base 88 is provided as a portion of the actuator or passive lock assembly, as shown in FIGS. 2, 3, and 10B. The base 88 is desirably provided adjacent the pair of pawls 74 and the U-shaped connector 76. A distal surface 90 of the pair of pawls 74 and the U-shaped connector 76 is desirably positioned against a proximal surface 92 of the base 88. The proximal surface 92 of the base desirably includes a plurality of posts 94.

Figure 11:
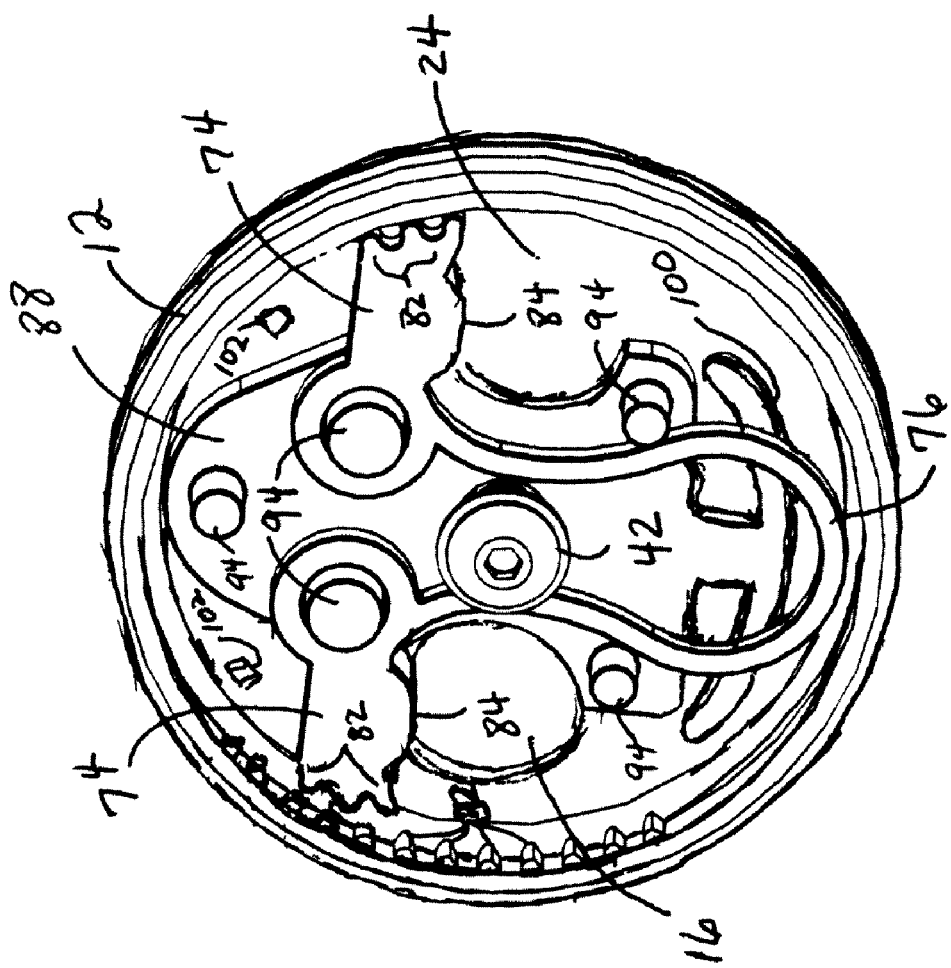
FIG. 11 is a perspective view of the proximal surface of the distal plate, with the pair of pawls and the base in their respective positions on the distal plate, showing the position of the pawls relative to the port, and particularly the position of the teeth of the pawls with respect to the teeth on the portion of the distal plate when no object is positioned through the port of the distal plate.
Figure 12:
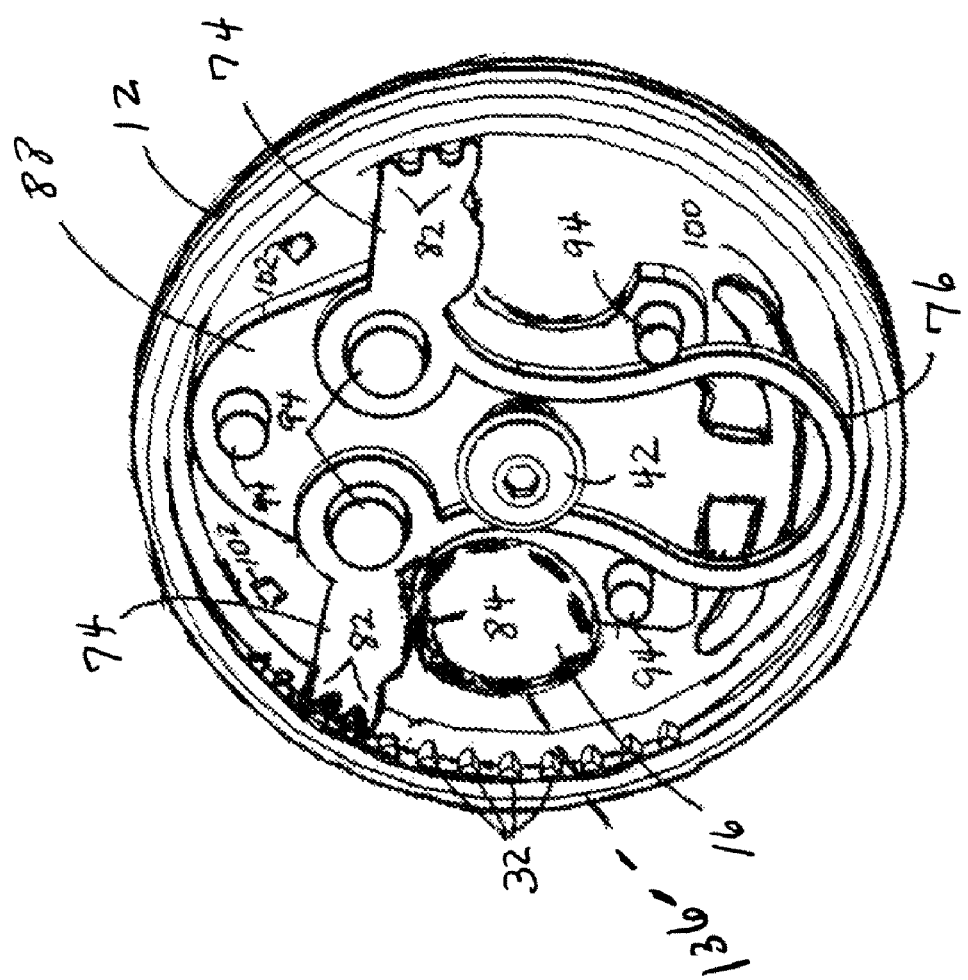
FIG. 12 is a perspective view of the proximal surface of the distal plate, with the pair of pawls and base in their respective positions on the distal plate, showing the position of one pawl relative to the port and the position of the teeth of the one pawl engaged with the teeth on the portion of the distal plate when an object (shown in cross section in the port via phantom lines) has displaced the one pawl.

Each circular portion 78 on each of the pair of pawls 74 is configured to be positioned over a post 94 on the proximal surface 92 of the base 88, as illustrated in FIGS. 11 and 12. The U-shaped connector 76 may also be positioned between two of the posts 94. In turn, each of the plurality of posts 94 is desirably positioned to fit within each of the plurality of circular ribs 70 on the distal surface 58 of the proximal plate 14, in order to hold the pair of pawls 74 and U-shaped connector 76 in a position adjacent the proximal plate 14 and to limit the movement of the pair of pawls 74. The base 88 includes an opening 95 therethrough, to permit passage of the fastener, i.e., such as a screw or pin 42, therethrough. A distal surface 96 of the base 88 includes a tab or stop 98 near the opening 95. One end of the base 88 includes a curved leg 100 which includes a tab 102 on the distal surface 96 of each end of the curved leg 100 (FIGS. 2 and 10B). The opposite end of the base 88 may include a circular groove 104 which is configured to hold an O-ring 106. The distal surface 96 of the base 88 is desirably positioned against the proximal surface 24 of the distal plate 12.

A collar 108 may be positioned over an outer surface 110 of the perimeter wall 66 of the proximal plate 14, as shown in FIGS. 2 and 3. The collar 108 may include a plurality of ribs 112 or other protuberances (not shown) on its outer surface 110 which assists a health care provider in holding the assembly 10 in the provider's hand and operating the assembly 10. The collar 108 desirably includes a pair of caps 114, each of which may be coupled to the collar 108 by a tether 116. Each cap 114 is configured to fit within a cuff, such as the first cuff 54 and/or the second cuff 62, to block or close the first port 50 and/or the second port 52. It will be understood that the caps 114 may be configured to fit within the cuffs 54, 62, over the cuffs 54, 62, screw or snap into or over the cuffs 54, 62, and so forth.

The term "couple" and variations thereof, desirably includes, but is not limited to, joining, connecting, fastening, linking, tying, adhering (via an adhesive), or associating two things integrally or interstitially together. It will be understood that two things may be coupled directly or indirectly together.

In operation, the cuff 20 of the port 16 may be coupled to a port in a manifold 120, which in turn is coupled to an endotracheal tube or artificial airway 122 and a ventilator (not shown). At least a portion of the artificial airway 122 is positioned in a portion of a patient's respiratory tract (not shown).

A suction catheter assembly 130, as partially illustrated in FIG. 1, includes at least a distal end connector 132 which desirably releaseably couples to the first cuff 54 of the first port 50 of the proximal plate 14. Alternatively, the suction catheter assembly 130 may be coupled to an intermediate quick release connector (not shown) which may be releaseably coupled to the first cuff 54. A sleeve 134 is desirably coupled to the distal end connector 132 and extends at least substantially over a suction catheter 136 and may include a proximal end connector (not shown) to substantially cover the suction catheter 154. The suction catheter 136 includes a distal tip with at least one opening therein (not shown). The terms "substantial" or "substantially" desirably, but not by way of limitation, refer to something which is done to a great extent or degree; a significant or great amount; for example, as used herein "substantially" as applied to "substantially covered" means that a thing is at least 70% covered.

The suction catheter 136 also desirably includes an elongated body 139 having a lumen therethrough and an open proximal end (not shown). The proximal end of the suction catheter 134 or the suction catheter assembly 130 is adapted to couple to at least a portion of a suctioning apparatus (not shown) which provides a suctioning force to the suction catheter 136. It will be appreciated that the suction catheter 136 has a length which is sufficient to extend through the assembly 10 and through any attached manifold 120 and artificial airway 122 so that it extends into a portion of a patient's respiratory tract in order to suction secretions therefrom. When the suction force is discontinued, it will be understood that the suction catheter 136 is then desirably withdrawn from the patient's respiratory tract, the artificial airway 122, the manifold 120, and the respiratory access assembly 10. The suction catheter 136 is desirably returned to its position in its assembly 130 and sleeve 134. In this manner, the substantial length of the suction catheter 136 is contained within the sleeve 134 and it is therefore positioned outside of the closed circuit ventilation system of the patient until needed again for suctioning secretions.

Suction catheters are well known and widely commercially available for many medical uses. Suctioning may be performed using an "open" or "closed" system. In the open system, the suction catheter is merely a flexible plastic tube that is inserted into the flexible lumen with a source of suction connected to the proximal end of the suction catheter. Anything that the suction catheter touches before entering the lumen must be maintained in a sterile condition so a "sterile field" must be created on or next to the patient. The suction catheter must be carefully handled after it is used since it will be coated with the patient's secretions. In contrast, in the "closed" system, for example that disclosed in U.S. Pat. No. 4,569,344, a device which may be used to suction secretions is enclosed within a generally cylindrical plastic bag to eliminate or minimize contamination of the suction catheter prior to use. This is generally referred to as a "closed suction catheter" and is available under the tradename TRACH CARE® from BALLARD® Medical Products (Kimberly-Clark Corporation). Closed suction systems are generally preferred by healthcare providers because they are less likely to spread infection to the patient and the healthcare provider. The present respiratory access port assembly 10 is desirably used with such a closed suction assembly 130.

It will be understood that the suction catheter assembly 130 may be coupled to either the first or the second cuff 54, 63 of the first or second ports 50, 52, respectively. Similarly, a bronchoscope, or other instrumentation, and so forth, may be releasably coupled to one of the first or second cuffs 54, 63 of the first or second ports 50, 52, respectively, as well. It will be appreciated that the suction catheter 136 and suction catheter assembly 130 are maintained as a part of the closed circuit ventilation system at all times.

In a method of operation and use, a health care provider grasps the manifold 120 which is coupled to the cuff 20 of the port 16 of the distal plate 12. The health care provider also grasps the collar 108 which is coupled to the outer surface 110 of the perimeter wall 66 of the proximal plate 14 and rotates the proximal plate 14 such that the cuff 20 and port 16 of the distal plate 12 aligns with the first cuff 54 and first port 50 of the proximal plate 14. The tab or stop 98 on the distal surface 96 of the base 88 is positioned within the semi-circular indentation 44 on the proximal surface 24 of the distal plate 12. The tab or stop 98 cooperates with the circular portion 78 to limit rotation of the distal and proximal plates 12, 14 to no more than about 200 degrees relative to each other. Therefore, if the ports 16, 50 and their respective cuffs 20, 54 are not aligned, a health care provider grasps the collar 108 and rotates the proximal plate 14 in a counterclockwise direction to its maximum point or rotation in order to permit alignment of the port 16 and cuff 20 of the distal plate 12 with the first port 50 and first cuff 54 of the proximal plate 14, as illustrated in FIG. 1. Alternatively, it will be understood that the proximal plate 14 may be held by a health care provider while the distal plate 12 may be moved to its maximum point of rotation in a clockwise direction. However, the distal plate 12 and its port 16 and cuff 20 are coupled to the manifold 120, which is coupled to a patient's artificial airway 122, all of which is desirably maintained in a relatively fixed position. Therefore, it will be understood that it is more desirable to hold the distal plate 12 stationary while rotating the proximal plate 14.

The phrase "stationary", "stationary plate" and/or "stationary disk" desirably, but not by way of limitation, refers to either the proximal plate or the distal plate when that plate, or component holding that plate, is grasped by a health care provider and held in a relatively fixed "stationary" position while the opposite disk is rotated to one of the three pre-determined positions by a health care provider. Both plates may be relatively "stationary plates" as well when the plates are positioned and locked together in a fixed, unmoving position.

The phrase "rotating plate" and/or "rotating disk" desirably, but not by way of limitation, refers to either the proximal plate or the distal plate when the plates are unlocked, so that each may rotate relative to the other. The distal and proximal plates are configured to be positioned in three pre-determined positions. When un-locked, however, both distal and proximal plates are free to rotate relative to each other, and each plate may move or rotate in a direction opposite (up to about 200 degrees or less) relative to each other. Both plates may move or "rotate" as well when the plates are positioned in the un-locked position so that each plate is free to be rotate in opposite directions by a health care provider.

When the ports 16, 50 and cuffs 20, 52 of the distal and proximal plates 12, 14, respectively, are in an alignment, they are releasably held in this specific, predetermined position by the cooperation of the pair of tabs 102 on the leg 100 of the distal surface 96 of the base 88 and two of the plurality of ramped indentations 46 on the proximal surface 24 of the distal plate 14. That is, each of the pair of tabs 102 on the leg 100 move into one of the plurality of ramped indentations 46. The tabs 102 on the distal surface 96 of the leg 100 are on the base 88, which is coupled to the proximal plate 14, while the plurality (four) of the indentations 46 are formed on the proximal surface 24 of the distal plate 12. Therefore, these components cooperate to releasably hold the distal and proximal plates 12, 14 in a specific, predetermined position, that is, a first open position (FIGS. 1 and 13). In the first open position the ports 16, 50 and cuffs 20, 54, respectively, are in an axially aligned position.

The term and phrase "open" and "open position" and variations thereof, desirably, but not by way of limitation, refers to a position of the aligned ports described herein to permit an object, such as a suction catheter, a portion of a bronchoscope, and so forth, move through the aligned ports and into a portion of a patient's respiratory tract.

Since the suction catheter assembly 130 is desirably coupled to the first cuff 54 of the first port 50, the suction catheter 134 may be advanced through the aligned ports 16, 50 and cuffs 20, 54, respectively, through the manifold 120 and the artificial airway 122 into at least a portion of a patient's respiratory tract to suction secretions therefrom. If a health care provider attempts to move the distal and proximal plates 12, 14 relative to each other into another position while the suction catheter (or other object) is positioned through the ports 16, 50 of the distal and proximal plates 12, 14, respectively, one or more components act to prevent movement of the plates 12, 14, thereby, providing a passive lock.

First, if the health care provider attempts to move the distal and proximal plates 12, 14 by grasping the manifold 120 and/or the distal plate 12, and holding it/them in a stationary position while simultaneously grasping the collar 108 and moving or rotating the proximal plate 14 in a counter-clockwise direction, such movement is prevented by the stop 98. The stop 98 on the base 88 (which is firmly coupled to the proximal plate 14) is positioned in the semi-circular indentation 44 on the proximal surface 24 of the distal plate 12. The semi-circular indentation 44 limits the rotation of the distal and proximal plates 12, 14 relative to each other. These components cooperate to prevent further rotation in a counter-clockwise direction.

Second, if the healthcare provider attempts to move or rotate the proximal plate 14 in a clockwise direction relative to the distal plate 12, the suction catheter 134 is pressed against the flange 84 of the pawl 74 which is adjacent the first port and first cuff 50, 54, respectively. This pressure moves the flange 84 and therefore the pawl 74, and causes at least some of the plurality of teeth 82 of the pawl 74 to engage at least some of the plurality of teeth 32 on the inner surface 30 of the perimeter wall 28 of the distal plate 12, as illustrated in FIG. 12. The teeth 82 of the pawl 74, which is coupled to the base 88 and to the proximal plate 14 via the base 88, engage and interlock with the teeth 32 of the distal plate 12. This engagement thereby substantially prevents clockwise movement of the proximal plate 14 relative to the distal plate 12. That is, while some very limited movement of the distal and/or proximal plate 12, 14 may occur, such movement does not substantially affect the alignment of the port 16 and first port 50 or the ability to move the suction catheter 134 through the ports 16, 50, because no substantial movement is allowed. Therefore a passive lock is provided by the cooperation of these components, which substantially prevents movement of the distal and proximal plates 12, 14. A health care provider is thereby prevented from inadvertently moving the distal and proximal plates 12, 14 when the suction catheter 136 is positioned through the aligned ports 15, 50. Such a move, absent such a passive safety lock, would be likely to guillotine a distal portion of the suction catheter 136, which could be catastrophic to the patient. This passive lock is disengaged when the suction catheter 136 is completely withdrawn from the aligned ports 16, 50 of the assembly 10, as illustrated in FIG. 11. This withdrawal permits the plurality of teeth 82 on the pawl 74 to move away from and disengage from the plurality of teeth 32 on the inner surface 30 of the perimeter wall 28 of the distal plate 12. Therefore, the proximal plate 14 is now permitted to rotate in a clockwise direction relative to the distal plate 12. Alternatively, it will be understood that the distal plate 12 may now also be rotated in a counter-clockwise direction relative to the proximal plate 14.

The assembly 10 may be moved into a second open position, illustrated in FIG. 14, when the proximal plate 14 is moved or rotated relative to the distal plate 12 (which is again desirably grasped in a relatively stationary position by the health care provider for reasons stated previously herein) in a clockwise direction to its maximum point or rotation in order to permit alignment of the port 16 and cuff 20 of the distal plate 12 with the second port 52 and second cuff 62 of the proximal plate 14. This position is a second selected, predetermined position, which provides an axial alignment of the ports 16, 52 and respective cuffs 20, 62 of the distal and proximal plates 12, 14. The tab or stop 98 on the distal surface 96 of the base 88 (which is coupled to the proximal plate 14) is positioned within the semi-circular indentation 44 on the proximal surface 24 of the distal plate 12. The stop 98 cooperates with the semi-circular indentation 44 to limit rotation of the distal and proximal plates 12, 14 to no more than about 200 degrees relative to each other. Therefore, the second position is as far as the healthcare provider can rotate the proximal plate 14 in the clockwise direction relative to the distal plate 12, since the stop 98 and the semi-circular indentation 44 cooperate to limit further rotation. When the ports 16, 52 and cuffs 20, 62 of the distal and proximal plates 12, 14, respectively, are in an axial alignment, they are releasably held in this specific, predetermined position by the cooperation of the pair of tabs 102 on the leg 100 of the distal surface 96 of the base 88 and two of the plurality of ramped indentations 46 on the proximal surface 24 of the distal plate 14. That is, each tab 102 on the leg 100 moves into one of the plurality of ramped indentations 46. The tabs 102 are on the base 88, which is coupled to the proximal plate 14. The two indentations 46 are formed on the proximal surface 24 of the distal plate 12. Therefore, these components cooperate to releasably secure the distal and proximal plates 12, 14 in another specific, predetermined position. That is, these components cooperate to secure the assembly 10 in the second open position. In this position, a bronchoscope, or other instrument or object, may be introduced through the aligned port 16 and second port 52 of the distal and proximal plates 12, 14 or the assembly 10, through the manifold 120, into the artificial airway 122 and into a portion of a patient's respiratory tract (not shown). It will be appreciated that, as described in detail above for the first open position, if a heath care provider attempts to move the distal and proximal plates 12, 14 while an object, such as, for example only, a portion of a bronchoscope is positioned through the aligned ports 16, 52 and cuffs 20, 62, respectively, the assembly 10 is positioned in a passive locked position which substantially prevents movement of the distal and proximal plates 12, 14.

The phrase "substantially prevent movement," and variations thereof, desirably, but not by way of limitation, refers to movement of the plates when a port of the distal plate is aligned with a port of the proximal plate, and an object is positioned through the aligned ports. The plates may have some slight movement which permits some slight misalignment, but the ports remain substantially aligned so that an object which is passed through the ports is not pinched off or closed by the slight misalignment, and the object may still be moved through the ports.

Again, one or more components, and desirably, but not by way of limitation, two components cooperate to prevent movement of the distal and proximal plates 12, 14, thereby again providing a passive lock for the assembly 10, when an object is positioned through the aligned port 16 and second port 52 of the distal and proximal plates 12, 14. First, if the health care provider attempts to move the distal and proximal plates 12, 14 by grasping the manifold 120 and/or the distal plate 12, and holding it/them in a stationary position while simultaneously grasping the collar 108 and moving or rotating the proximal plate 14 in a clockwise direction, such movement is prevented by the stop 98. The stop 98 on the base 88 (which is firmly coupled to the proximal plate 14) is positioned in the semi-circular indentation 44 on the proximal surface 24 of the distal plate 12. The semi-circular indentation 44 limits over-rotation of the distal and proximal plates 12, 14 relative to each other. These components cooperate to prevent further rotation of the proximal plate 14 in the clockwise direction.

Second, if the healthcare provider attempts to move or rotate the proximal plate 14 in a counter-clockwise direction relative to the distal plate 12 when the ports 16, 52 of the distal and proximal plates 12, 14, respectively are aligned, the portion of the bronchoscope or object (not shown) is pressed against the flange 84 of the pawl 74 which is adjacent the second port 52 and second cuff 62. This pressure moves the flange 84 and its pawl 74, and causes at least some of the plurality of teeth 82 of the pawl 74 to engage at least some of the plurality of teeth 32 on the inner surface 30 of the perimeter wall 28 of the distal plate 12, as illustrated in FIG. 12. The teeth 82 of the pawl 74, which is coupled to the proximal plate 14, engage and interlock with the teeth 32 of the distal plate 12, thereby substantially preventing counter-clockwise movement of the proximal plate 14 relative to the distal plate 12. That is, while some very limited movement of the distal and/or proximal plate 12, 14 may occur, such movement does not substantially affect the alignment of the ports 16, 52 or the ability to move the suction catheter 134 through the ports 16, 52, because no substantial movement is allowed. Therefore a passive lock is provided by the cooperation of these components, which substantially prevents movement of the distal and proximal plates 12, 14.

A health care provider is thereby prevented from inadvertently moving the distal and proximal plates 12, 14 when an object, such as a bronchoscope, a suction catheter, and so forth, is positioned through the aligned port 16 and second port 52. Such a move, absent such a passive safety lock, would be likely to affect an object, for example, guillotine a distal portion of such an object, which again could be catastrophic to the patient. This passive lock is removed when the object (illustrated in FIG. 12 as a suction catheter 136) is completely withdrawn from the aligned ports 16, 52 of the distal and proximal plates 12, 14 of the assembly 10. This withdrawal permits the teeth 82 on the pawl 74 to move away from and disengage from the teeth 32 on the inner surface 30 of the perimeter wall 28 of the distal plate 12, as shown in FIG. 11. Therefore, the proximal plate 14 is now permitted to rotate in a counter-clockwise direction relative to the distal plate 12. Alternatively, it will be understood that the distal plate 12 may also be rotated in a clockwise direction relative to the proximal plate 14.

The first position with alignment of port 16 and cuff 20 with the first port 50 and first cuff 54 are desirably positioned, for example, but not by way of limitation, about 180 degrees apart from the second position, with alignment of port 16 and cuff 20 with second port 52 and second cuff 62 (FIG. 13). When the assembly 10 is positioned in the first position, the second port 52 and second cuff 62 are desirably blocked by a portion of the distal plate 12. Similarly, when the assembly 10 is position in the second position, the first port 50 and first cuff 54 are also desirably blocked by a portion of the distal plate 12 (FIG. 14). Such blocking cooperates with other components, such as caps 114, and so forth, to maintain PEEP pressure and to prevent confusion over which port is open by preventing introduction of an object, such as a suction catheter, bronchoscope, and so forth, into the blocked port.

The respiratory access assembly 10 may also include an additional predetermined position, such as a third selected position, as shown in FIG. 15. That is, the assembly 10 may include a third position which is a closed position for all ports 16, 50 and 52 of the distal and proximal plates 12, 14. In this instance, but not by way of limitation, the closed position is provided between the first open position and the second open position. Therefore, the closed position is a position, for example, at about a 90 degree angle relative to the first position and the second position. When a health care provider moves or rotates the proximal plate 14 relative to the distal plate 12 between first and second open positions, the distal and proximal plates 12, 14 are moved through the intermediate closed position. This third closed position is an optional position, since there is no danger of guillotining any portion of an object positioned in a port, since no ports are aligned to permit an object to be passed therethrough. This position may be utilized when no objects are positioned through any of the ports 16, 50, 52. In the third position, the manifold 120 and/or a portion of the distal plate 12 is desirably held in a relatively stationary position, while the health care provider moves or rotates the proximal port either counter-clockwise (if the distal and proximal plates 12, 14 were in the first position) or counter-clockwise (if the distal and proximal plates 12, 14 were in the second position), until the port 16 of the distal plate 12 is positioned between the first port 50 and the second port 52. The port 16 is then desirably position on the O-ring contained in the groove 104 on the distal surface 96 of the base 88, which blocks and acts to seal the port 16. In this position, a portion of the distal plate 12 blocks both the first port 50 and the second port 52. The ports 16, 50 and 52 are not locked in this position. However, the ports 16, 50, and 52 are releasably held in the selected, predetermined third closed position by the cooperation of the pair of tabs 102 on the leg 100 of the distal surface 96 of the base 88 and two of the plurality of ramped indentations 46 on the proximal surface 24 of the distal plate 14. Again, each of the pair of tabs 102 on the leg 100 move into one of the plurality of ramped indentations 46. The tabs 102 are on the base 88, which is coupled to the proximal plate 14. The two ramped indentations 46 are formed on the proximal surface 24 of the distal plate 12. Therefore, these components cooperate to releasably secure the distal and proximal plates 12, 14 into the third closed position. It will be understood that the ramped indentations hold the distal and proximal plates 12, 14 in a position until sufficient pressure is applied by a health care provider to move or rotate one or both plates 12, 14, at which time the ramps on the indentations 46 permit the tabs 102 to move out of the indentations 46. The health care provider may choose to move the plates 12, 14 into the third closed position to assist in maintaining PEEP when the ports 16, 50, and 52 will not be used for a period of time.

The term and/or phrase "closed" or "closed position" and variations thereof, desirably, but not by way of limitation, refers to a position of one or more ports in which the port(s) are not aligned, so that no large object, such as a suction catheter, a portion of a bronchoscope, and so forth, may move through the referenced "closed" port(s). A port may be "closed" or "blocked" such that an object, such as those referenced previously, are blocked or prevented from moving through the port(s). The port may not be totally blocked or closed, however, and gases and/or liquid may, in at least some instances, continued to move through a blocked or closed port.

Certain components herein have been described and shown at certain angles. However, it will be understood that any component may be positioned at any angle or any combination of angles, so long as the assembly operates as shown and/or described herein.

It will also be understood that curved or arched plates, convex or concave disks or plates, or flat or planar disks or plates may be used herein. Further, the disks or plates may comprise any configuration, so long as they operate as shown and/or described herein. Similarly, the disks or plates may move in varying ways, that is, the disks or plates may rotate, pivot, slide, and move in any manner, and so forth, relative to each other, so long as they operate to achieve the result(s) as shown and/or described herein.

If the distal and proximal plates are flat, square or rectangular plates (not shown), it will be appreciated that the distal and proximal plates may be positioned to slide relative to each other. In such an embodiment, but not by way of limitation, the base and pawls may be configured differently to accommodate sliding, and more than one base may be provided with one or more pawls. More than one stop may be provided to limit the movement of the plates relative to each other. The distal plate may have more than one line of teeth. The distal and/or proximal plate may have one or more, fingers, teeth, grooves, rails, ribs, and so forth. That is, the distal and/or proximal plate may have structural features which permit an interlock with each other. One skilled in the art will understand the modifications which will be required to implement this and other alternative embodiments.

Further, it will be appreciated that a rod, block, or any device known in the art, and so forth, may take the place of the pawl. Such a device would be movable so that it may be frictionally positioned against a portion of a plate wall to prevent movement of at least one plate relative to the other. Such a plate wall may itself contain a roughened area or frictional elements, such as teeth, bars, and so forth. Alternatively, the plate wall may include a frictional component, such as at least a portion of an O-ring, ribs, teeth, and so forth, in which the device would be frictionally positioned against to prevent movement of at least one plate.

The assembly 10 may include more than one port and cuff on the distal disk or plate, and more than two ports and cuffs on the proximal disk or plate (not shown). In addition, the assembly 10 may include the manifold 120, or any other manifold known in the art. Further, the assembly 10 may include a suction catheter assembly 130, or any other suction catheter assembly known in the art. In a further alternative, the assembly 10 may include both a manifold as well as a suction catheter assembly.

The phrase "operable communication" desirably, but not by way of limitation, refers to a transmission or passage between two points and/or two structures for a specific purpose. In this example, operable communication would be a passage which permits gasses and/or liquid(s) to pass, and may also be configured to permit objects to pass.

The terms "comprise," "comprises," "comprising" and other derivatives from the root term "comprise" desirably, but not by way of limitation, are intended to be open-ended terms that specify the presence of any stated features, elements, integers, steps, or components, but do not preclude the presence or addition of one or more other features, elements, integers, steps, components, or groups thereof. Similarly, the terms "include", "includes", "including," as well as the terms "has", "have", "having", "is" and derivatives thereof, are intended to be interpreted as the word "comprise", and are intended to be open-ended terms that specify the presence of any stated features, elements, integers, steps, or components, but do not preclude the presence or addition of one or more other features, elements, integers, steps, components, or groups thereof.

While the present invention has been described in connection with certain preferred embodiments it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. A respiratory access assembly, comprising:
   a distal plate having a port, the port adapted to be positioned in operable communication with an artificial airway of a patient;
   a proximal plate including a first port and a second port, the distal plate positioned against the proximal plate in a stacked configuration, each plate configured to move; and
   an actuator positioned adjacent to at least one plate, the actuator cooperating with both plates to substantially prevent movement of the plates when the port of the distal plate is positioned in an alignment with at least one port of the proximal plate and an object is positioned through the aligned ports of the plates, the actuator cooperating with at least one plate to permit movement of at least one plate when (a) no object is positioned through aligned ports, and (b) when no ports are aligned, wherein the actuator is activated only when an object is positioned through the aligned ports to substantially prevent movement of the plates, thereby providing a passive lock; and,
   wherein at least a portion of the actuator is coupled to one plate and includes a pawl with teeth, a portion of the pawl positioned adjacent at least one port, such that when an object is positioned through the port, the object moves the portion of the pawl such that at least a portion of the teeth of the pawl engage at least a portion of teeth on another plate, thereby substantially preventing movement of the plates in at least one direction until the object is withdrawn so that the portion of the pawl moves back to its initial position adjacent the port and the teeth of the pawl disengage from the teeth of the plate.

2. The respiratory access assembly of claim 1, wherein the actuator includes a stop provided on a base coupled to one plate, the stop configured to move within the confines of an indentation formed on an opposing plate, both of which cooperate to substantially prevent movement of the plates in at least one direction.

3. The respiratory access assembly of claim 1, wherein when the port of the distal plate and the first port of the proximal plate are aligned, the assembly is positioned in a first open position, and the actuator is activated to substantially prevent movement of the plates when an object is positioned through the aligned ports.

4. The respiratory access assembly of claim 3, wherein when the assembly is positioned in the first position, the second port in the proximal plate is blocked by a portion of the distal plate.

5. The respiratory access assembly of claim 1, wherein when the port of the distal plate and the second port of the proximal plate are aligned, the assembly is positioned in a second open position, and the actuator is activated to substantially prevent movement of the plates when an object is positioned through the aligned ports.

6. The respiratory access assembly of claim 5, wherein when the assembly is positioned in the second first position, the first port in the proximal plate is blocked.

7. The respiratory access assembly of claim 1, wherein when the port of the distal plate is positioned between the first port and the second port of the proximal plate, no ports are aligned and the assembly is positioned in a third closed position such that each port is blocked.

8. The respiratory access assembly of claim 1, wherein the distal plate includes a plurality of ramped indentations and the proximal plate includes a base having at least one tab, wherein when the assembly is positioned in one of a plurality of predetermined positions, the tab is positioned in one of the plurality of ramped indentations to releasably to hold the each plate in one of the predetermined positions.

* * * * *